(12) United States Patent
Shin et al.

(10) Patent No.: US 11,547,389 B2
(45) Date of Patent: Jan. 10, 2023

(54) METHODS AND SYSTEMS FOR ULTRASOUND CONTRAST ENHANCEMENT

(71) Applicant: KONINKLIJKE PHILIPS N.V., Eindhoven (NL)

(72) Inventors: Jun Seob Shin, Medford, MA (US); Harold Agnes Wilhelmus Schmeitz, Eindhoven (NL); Frederik Jan De Bruijn, Eindhoven (NL); Francois Guy Gerard Marie Vignon, Andover, MA (US); Sheng-Wen Huang, Ossining, NY (US); Andrew Hancock, Sacramento, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 144 days.

(21) Appl. No.: 16/647,833

(22) PCT Filed: Sep. 13, 2018

(86) PCT No.: PCT/EP2018/074690
§ 371 (c)(1),
(2) Date: Mar. 16, 2020

(87) PCT Pub. No.: WO2019/057592
PCT Pub. Date: Mar. 28, 2019

(65) Prior Publication Data
US 2020/0214677 A1    Jul. 9, 2020

Related U.S. Application Data

(60) Provisional application No. 62/562,093, filed on Sep. 22, 2017.

(51) Int. Cl.
*A61B 8/08* (2006.01)
*G01S 7/52* (2006.01)
*G01S 15/89* (2006.01)

(52) U.S. Cl.
CPC ........ *A61B 8/5207* (2013.01); *G01S 7/52047* (2013.01); *G01S 15/8927* (2013.01)

(58) Field of Classification Search
CPC ............ G01S 15/8927; G01S 7/52047; A61B 8/5207; G10K 11/346
See application file for complete search history.

(56) References Cited

U.S. PATENT DOCUMENTS 5,903,680 A * 5/1999 De Haan ................. H04N 5/21
                                                         382/265
6,443,896 B1    9/2002 Detmer
(Continued)

FOREIGN PATENT DOCUMENTS

WO    WO-2015087191 A1 *  6/2015  ............... A61B 8/12
WO    2019057461 A1    3/2019

OTHER PUBLICATIONS

J. Shin et al., "Synergistic Enhancements of Ultrasound Image Contrast With a Combination of Phase Aberration Correction and Dual Apodization With Cross-Correlation", IEEE Transactions on Ultrasonics, Ferroelectrics, and Frequency Control, vol. 59, No. 9, pp. 2089-2101, Sep. 2012 (Year: 2012).*
(Continued)

*Primary Examiner* — Joel Lamprecht
*Assistant Examiner* — Nyrobi Celestine

(57) ABSTRACT

Systems and methods for suppressing off-axis sidelobes and/or clutter, near-field reverberation clutter, and/or grating lobe contributions are disclosed. A dual apodization with median (DAM) filtering technique is disclosed. The dual apodization technique may include summing aligned channel data with apodization functions (406, 412, 414) with
(Continued)

complementary apertures applied. Median values for a zero function (RF3) and the resulting signals (RF1, RF2) from the complementary apertures are determined to generate a median value signal (416, MVS). The median value signal is used to generate an ultrasound image with enhanced image contrast. A method of image smoothing of the ultrasound image with enhanced image contrast is also disclosed. The smoothed image may include low frequency components of the ultrasound image with enhanced image contrast and high frequency components of an original image.

20 Claims, 9 Drawing Sheets

(56) References Cited

U.S. PATENT DOCUMENTS

| | | | | |
|---|---|---|---|---|
| 6,530,885 | B1 | 3/2003 | Entrekin | |
| 7,826,308 | B2* | 11/2010 | Song | G01S 7/52047 367/87 |
| 2009/0141957 | A1 | 6/2009 | Yen | |
| 2012/0143059 | A1* | 6/2012 | Magee | G01S 7/52047 600/447 |
| 2013/0109968 | A1* | 5/2013 | Azuma | A61B 8/5269 600/441 |
| 2016/0089112 | A1* | 3/2016 | Rosado-Mendez | B06B 1/0215 600/459 |
| 2016/0354062 | A1* | 12/2016 | Hwang | A61B 8/5207 |
| 2016/0367224 | A1 | 12/2016 | Yamamoto | |
| 2017/0108584 | A1* | 4/2017 | Oelze | G01S 7/52047 |

OTHER PUBLICATIONS

International Search Report & Written Opinion of PCT/EP2018/074690, dated Dec. 18, 2018.

Seo, Chi Hyung et al, "Sidelobe Suppression in Ultrasound Imaging using dual Apodization with Cross-Correlation", IEEE Transactions on Ultrasonics Ferroelectrics and Frequency Control, vol. 55, No. 10, pp. 2198-2210. Oct. 2008.

Shin, Jun Seob et al "Robust Ultrasonics Reverberation clutter Suppression using Multi-Apodization with Cross-Correlation", 2014 IEEE International Ultrasonics Symposium, pp. 543-546.

Seo, Chi Hyung et al "Evaluating the Robustness of Dual Apodization with Cross-Correlation", IEEE Transactions on Ultrasonics Ferroelectrics and Frequency Control, vol. 56, No. 2, pp. 291-303, Feb. 2009.

Stankwitz, H. C. et al, "Nonlinear apodization for side lobe control in SAR imagery", IEEE Transactions on Aerospace and Electronic Systems, vol. 31, No. 1, pp. 23-52, Jan. 1995.

\* cited by examiner

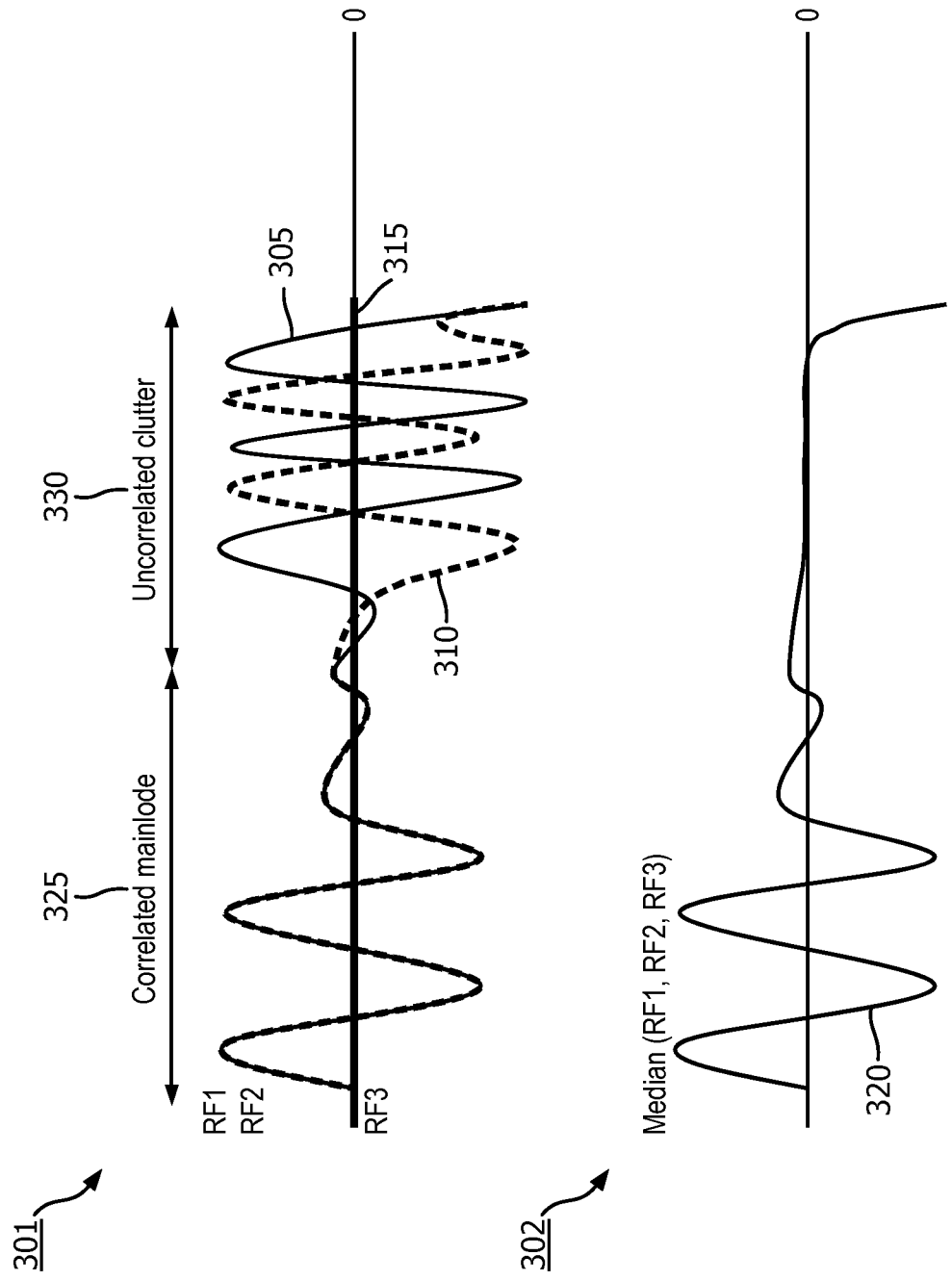

METHODS AND SYSTEMS FOR ULTRASOUND CONTRAST ENHANCEMENT

RELATED APPLICATION

This application claims the benefit of and priority to U.S. Provisional No. 62/562,093, filed Sep. 22, 2017, which is incorporated by reference in its entirety.

TECHNICAL FIELD

This application is directed to dual apodization with median filtering techniques. Specifically, this application is directed to dual apodization with median filtering for contrast enhancement in ultrasound images.

BACKGROUND

In medical ultrasound, image contrast is often compromised as a result of acoustic clutter due to off-axis scattering, reverberation clutter due to near-field anatomical structures, and random electronic noise. In order to address this problem, several adaptive weighting techniques have been proposed in the medical ultrasound community.

Well-known adaptive weighting techniques such as the coherence factor (CF), the generalized coherence factor (GCF), the phase coherence factor (PCF) and the short-lag spatial coherence (SLSC) technique have been proposed, but they all require access to per-channel data to compute a weighting mask, which is used to weigh down the contributions from acoustic clutter and reverberation clutter from the original image. The required access to per-channel data may make hardware implementations of these techniques difficult, especially on pre-existing ultrasound systems.

SUMMARY

The systems, methods, and/or apparatuses described herein may provide improvements over previous adaptive weighting techniques and/or other dual apodization techniques. The dual apodization with median (DAM) technique described herein may utilize two complementary apertures which may reduce and/or suppress off-axis signals. An aperture shift introduced by complementary apodizations may cause off-axis signals to be out of phase between the two apertures. Taking the median signal between the two apertures and a zero value may reduce and/or eliminate signals that are out of phase between the two apertures. Signals out of phase between the two apertures may be off-axis signals that may contribute to decreased image contrast. Thus, reduction and/or elimination of these out of phase signals may provide improved image contrast.

As described herein, the DAM technique may filter out undesired clutter contributions by taking the median value of the three values at each position: 1) the radio frequency (RF) signal from an odd aperture; 2) the RF signal from an even aperture; and 3) the RF signal=0 or near 0 (e.g., 0.1, 0.01, 0.001). The terms even and odd apertures as used herein refer to complementary apertures. This technique may eliminate the need to access per-channel data and/or to perform cross-correlation computation with a predetermined two-dimensional kernel, and other image processing steps on the weighting mask such as thresholding and spatial smoothing, all of which are associated with at least one or more parameters that must be optimized empirically.

According to an exemplary embodiment of the disclosure, a method may include generating a first signal equivalent to summing aligned channel data with an apodization function with a first aperture applied, wherein the aligned channel data corresponds to ultrasound data, generating a second signal equivalent to summing the aligned channel data with the apodization function with a second aperture applied, wherein the second aperture is complementary to the first aperture, determining median values of the first signal, the second signal, and a third signal to generate a median value signal, wherein the third signal is constant value signal, wherein the constant value is zero or near zero, and generating an ultrasound image, based at least in part, on the median value signal.

According to some exemplary embodiments of the disclosure, the method may further include generating an original image from the aligned channel data, applying a first spatial low pass filter to the original image to generate a low frequency original image, subtracting the low frequency original image from the original image to generate a high frequency original image, applying a second spatial low pass filter to the ultrasound image to generate a low frequency ultrasound image, and summing the high frequency original image and the low frequency ultrasound image to generate a final image.

According to another exemplary embodiment of the disclosure, an ultrasound imaging system may include an ultrasound transducer array which may be configured to transmit and receive ultrasound signals, a plurality of channels operatively coupled to the ultrasound transducer which may be configured to transmit channel data based, at least in part, on the received ultrasound signals, a beamformer operably coupled to the plurality of channels, the beamformer may be configured to align the channel data, and a signal processor operatively coupled to the beamformer. The signal processor may be configured to receive aligned channel data from the beamformer, generate a first signal equivalent to the aligned channel data summed with an apodization function with a first aperture applied, generate a second signal equivalent to the aligned channel data summed with the apodization function with a second aperture applied, wherein the second aperture is complementary to the first aperture, determine median values of the first signal, the second signal, and a third signal to generate a median value signal, wherein the third signal is a constant value signal, wherein the constant value is zero or near zero, and generate an ultrasound image, based at least in part, on the median value signal.

BRIEF DESCRIPTION OF THE DRAWINGS

FIG. 3 illustrates a plot of an example of channel data after passing through an odd apodization function, an even apodization function, and a zero value function and a plot of a median of the three apodization functions according to embodiments of the present disclosure.

DETAILED DESCRIPTION

Figure 1:
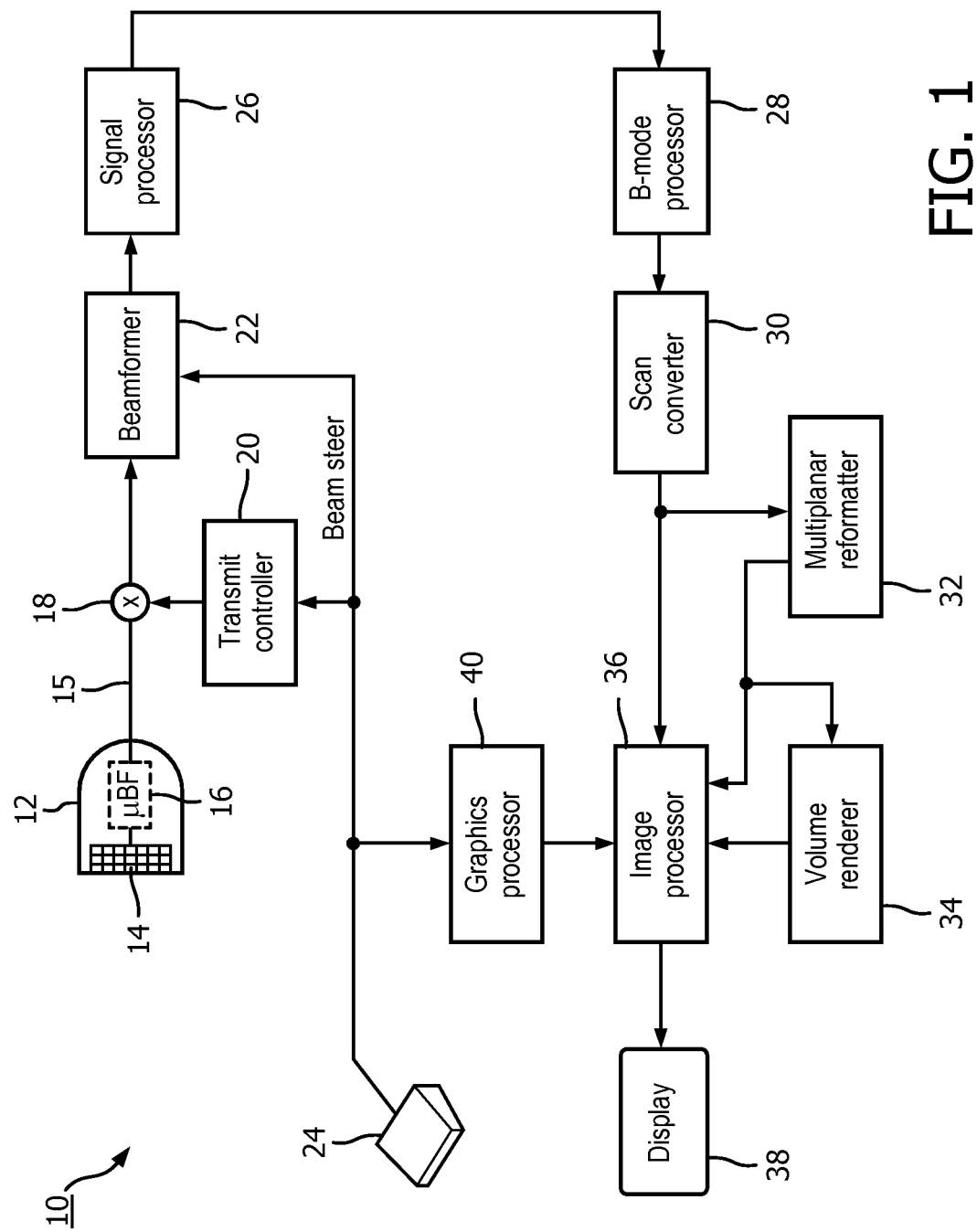
FIG. 1 is a block diagram of an ultrasound imaging system according to principles of the present disclosure.

The following description of exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

Apodization-based adaptive weighting techniques may generate weighting masks without having access to the per-channel data and may be easier to implement from a hardware perspective compared to other adaptive weighting techniques. For example, a technique called the dual apodization with cross-correlation (DAX) applies a dual-apodization function followed by cross-correlation of the two functions. An example of a DAX technique may be found in C. H. Seo, and J. T. Yen, "Sidelobe suppression in ultrasound imaging using dual apodization with cross-correlation", *IEEE Trans. Ultrason. Ferroelectr. Freq. Control*, vol. 55, no. 10, 2198-2210, October 2008. However, DAX techniques require additional cross-correlation computations with a pre-determined two-dimensional kernel, and image processing of the weighting mask such as thresholding and spatial smoothing. In addition to high computational load, all of the image processing steps of the DAX method require setting at least one parameter that must be optimized empirically. Empirical optimization may require extensive experiments by an ultrasound system developer and/or an end user (e.g., ultrasound technician, clinician) prior to imaging. In some cases, empirical optimization may require subjective determinations by a human user, which may be time consuming and/or introduce inconsistencies in performance between users.

According to principles of the present disclosure, a filtering technique called dual apodization with median (DAM) may reduce and/or eliminate noise in ultrasound images including noise contributions from off-axis sidelobes/clutter, near-field reverberation clutter, and/or grating lobes. The DAM technique may be performed in the beam-space domain by taking the median value of three values at each position in an ultrasound image: the radio frequency (RF) signals from two complementary apertures (e.g., an odd aperture and an even aperture) and a zero signal or near-zero signal. The DAM technique may not require significant additional hardware implementation. The DAM technique may eliminate the need to perform cross-correlation computation and/or additional image processing steps. This may improve image processing time and/or reduce hardware requirements of an imaging system.

As described herein, an ultrasound imaging system according to principles of the disclosure may include an ultrasound transducer array which may be configured to transmit and receive ultrasound signals. A plurality of channels may be operatively coupled to the ultrasound transducer. The channels may be configured to transmit channel data based, at least in part, on the received ultrasound signals (e.g., echos). The channel data may be radio frequency (RF) data in some embodiments. A beamformer may be operably coupled to the plurality of channels and configured to align the channel data. Alignment may include delaying and/or geometrically aligning the channel data from the channels. A signal processor may be operatively coupled to the beamformer. The signal processor may be configured to receive aligned channel data from the beamformer, generate a first signal equivalent to the aligned channel data summed with an apodization function with a first aperture applied and generate a second signal equivalent to the aligned channel data summed with the apodization function with a second aperture applied. The second aperture may be complementary to the first aperture. The signal processor may determine median values of the first signal, the second signal, and a third signal to generate a median value signal. The third signal may be a constant value signal. The constant value may be zero or near zero. The signal processor may generate an ultrasound image, based at least in part, on the median value signal. This ultrasound image may have improved contrast compared to an ultrasound image generated by applying only a rectangular apodization function.

Referring to FIG. 1, an ultrasound imaging system 10 constructed in accordance with the principles of the present disclosure is shown in block diagram form. In the ultrasonic diagnostic imaging system of FIG. 1, an ultrasound probe 12 includes a transducer array 14 for transmitting ultrasonic waves and receiving echo information. A variety of transducer arrays are well known in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. The transducer elements of transducer array 14 may be coupled via channels 15 to a microbeamformer 16 in the probe 12 in some embodiments. A separate channel may be provided for each transducer element of the transducer array 14 or for each patch of transducer elements. However, for clarity of the diagram, only one line is illustrated for the channels 15 in FIG. 1. The microbeamformer 16 may control transmission and reception of signals by the transducer elements in the array. In this example, the microbeamformer 16 is coupled by the probe cable to a transmit/receive (T/R) switch 18, which switches between transmission and reception and protects the main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by the transmit controller 20 coupled to the T/R switch 18 and the beamformer 22, which receives input from the user's operation of the user interface or control panel 24. One of the functions controlled by the transmit controller 20 is the direction in which beams are steered. Beams may be steered straight ahead from (orthogonal to) the transducer array, or at different angles for a wider field of view. The microbeamformer 16 may perform some alignment (e.g., delay and/or geometric alignment) of the radio frequency (RF) signals (e.g., channel data) from the channels 15. The signals produced by the microbeamformer 16 may be coupled to a main beamformer 22 for further alignment.

In some embodiments, the microbeamformer 16 is omitted. The transmit controller 20 may control the transducer array 14 directly through the T/R switch 18. Data from the transducer array 14 elements may be transmitted via channels 15 to the main beamformer 22 for alignment.

The channel data aligned by the beamformer 22 are coupled to a signal processor 26. The signal processor 26 can process the aligned channel data in various ways, such as bandpass filtering, decimation, I and Q component separation, and harmonic signal separation. The signal processor 26 may also perform additional signal enhancement such as speckle reduction, signal compounding, and noise elimination. According to principles of the present disclosure, the signal processor may perform a dual apodization with median (DAM) filtering technique on the channel data aligned by the beamformer 22. The signal processor 26 may be implemented in hardware (e.g., Application Specific Integrated Circuit (ASIC)), software, or a combination thereof. Although shown as a single unit in FIG. 1, in some embodiments, the signal processor 26 may be implemented with multiple processors.

The processed signals generated by the signal processor 26 are coupled to a B mode processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.) The 2D or 3D images are coupled from the scan converter 30, multiplanar reformatter 32, and volume renderer 34 to an image processor 36 for further enhancement, buffering and temporary storage for display on an image display 38. The graphics processor 40 can generate graphic overlays for display with the ultrasound images. These graphic overlays can contain, e.g., standard identifying information such as patient name, date and time of the image, imaging parameters, and the like. For these purposes the graphics processor receives input from the user interface 24, such as a typed patient name. The user interface can also be coupled to the multiplanar reformatter 32 for selection and control of a display of multiple multiplanar reformatted (MPR) images.

Returning to the DAM filtering technique, which may be performed by a signal processor (e.g., signal processor 26) or processors, a method according to principles of the present disclosure may include generating a first signal equivalent to summing aligned channel data with an apodization function with a first aperture applied. The aligned channel data may correspond to ultrasound data. The method may further include generating a second signal equivalent to summing the aligned channel data with the apodization function with a second aperture applied, which may be complementary to the first aperture. The method may further include determining median values of the first signal, the second signal, and a third signal to generate a median value signal. The third signal may be a constant value signal, which may be zero or near zero. The method may further include generating an ultrasound image, based at least in part, on the median value signal.

In some embodiments, additional steps may be performed as part of the method, which may include generating an original image from the aligned channel data, applying a first spatial low pass filter to the original image to generate a low frequency original image, subtracting the low frequency original image from the original image to generate a high frequency original image, applying a second spatial low pass filter to the ultrasound image to generate a low frequency ultrasound image, and summing the high frequency original image and the low frequency ultrasound image to generate a final image. This may produce an image with improved contrast that retains details such as speckle pattern from the original image.

Figure 2:
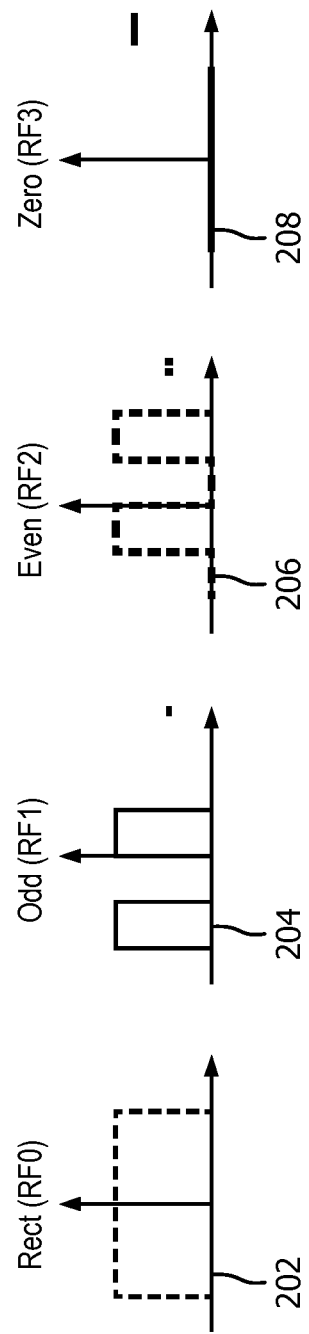
FIG. 2 illustrates examples of four apodization functions according to principles of the present disclosure.

FIG. 2 illustrates examples of four apodization functions 202, 204, 206, and 208 according to principles of the present disclosure. Apodization functions determine the weight given to data from each channel during summing to generate a beamsum signal. As mentioned previously in reference to FIG. 1, each channel may correspond to a transducer element in a transducer array. The rectangular Rect apodization function 202 gives equal weight to all channels. Thus, in some embodiments, the signal from each transducer element is equally weighted. At the opposite end of the spectrum, the Zero apodization function 208 gives no weight (e.g., masks) the data from all of the channels. With the Zero apodization function 208, all transducer elements may be masked (e.g., off). Apodization functions Odd 204 and Even 206 alternate in weighting some channels while masking others. Apodization function Odd 204 may be generated by applying an odd aperture to an apodization function and apodization function Even 206 may be generated by applying an even aperture to an apodization function. In some embodiments, such as the examples shown in FIG. 2, the odd and even apodization functions may uniformly weight all of the channels not masked. The apodization function with an odd aperture 204 may weight the opposite channels as the apodization function with an even aperture 206. For example, the apodization function 204 may weight odd numbered channels and mask even numbered channels while the apodization function 206 may weight even numbered channels and mask odd numbered channels.

Although odd and even channels or transducer elements are used as examples, the terms "odd" and "even" apodization functions as used herein refer to two complementary apodization functions and do not necessarily correspond to odd or even numbered channels and/or transducer elements. Furthermore, the even and odd aperture apodization functions are not limited to alternating between single channels, but may alternate between groups of multiple channels (e.g., two, three, four). The multiple channels may be adjacent (e.g., consecutive) to one another. This may correspond to transducer elements that are adjacent to one another in some embodiments. Alternating between single channels may correspond to an apodization function having a short period whereas the period of the apodization function becomes longer as the number of multiple channels included in the groups increases. As the period of the even and odd apodization functions increase, the resulting DAM filtering will become more aggressive. The period may be pre-set in an ultrasound imaging system and/or may be selected by a user via a user interface (e.g., user interface 24).

FIG. 3 illustrates a plot 301 of an example of aligned channel data after passing through an odd apodization function and an even apodization function. Plot 301 further includes a constant zero function. FIG. 3 further illustrates a plot 302 of a median of the signals generated by the three functions. In some embodiments, the aligned channel data may have been provided by a beamformer (e.g., beamformer 22) to a signal processor (e.g., signal processor 26), which may have summed the aligned channel data with the apodization functions and/or performed the median operation. According to principles of the present disclosure, when a complementary pair of apertures (e.g., odd and even) are applied to apodization functions to form two independent beamsum RF signals (RF1 305 and RF2 310 in FIG. 3) from the channel data, they may be highly correlated if the signals are from the on-axis mainlobe, as shown in the correlated mainlobe region 325. However, the signals may be highly uncorrelated if the signals are from off-axis regions, as shown in the uncorrelated clutter region 330. This is because the odd and even apertures have a large effective pitch, introducing grating lobes that have a phase difference of half a wavelength. The periods of the even and odd apodization functions, in addition to adjusting the aggressiveness of the filter, may also change the position of the introduced grating lobes.

After introducing a third signal RF3 315, which is zero or near zero for all values, a new RF signal (e.g., median value signal) 320 may be obtained by taking the median value of RF1 305, RF2 310, and RF3 315. In the correlated mainlobe region 325, median value signal 320 results in a new signal very similar to RF1 305 or RF2 310. In the uncorrelated clutter region 330, median value signal 320 results in a signal padded with zeroes. This may reduce noise in an image generated from the median signal. If the phase difference between RF1 and RF2 is between 0° and 180°, median value signal 320 may produce a new signal which is smaller in amplitude when compared with RF1 305 and RF2 310 but may not resemble either.

Figure 4A:
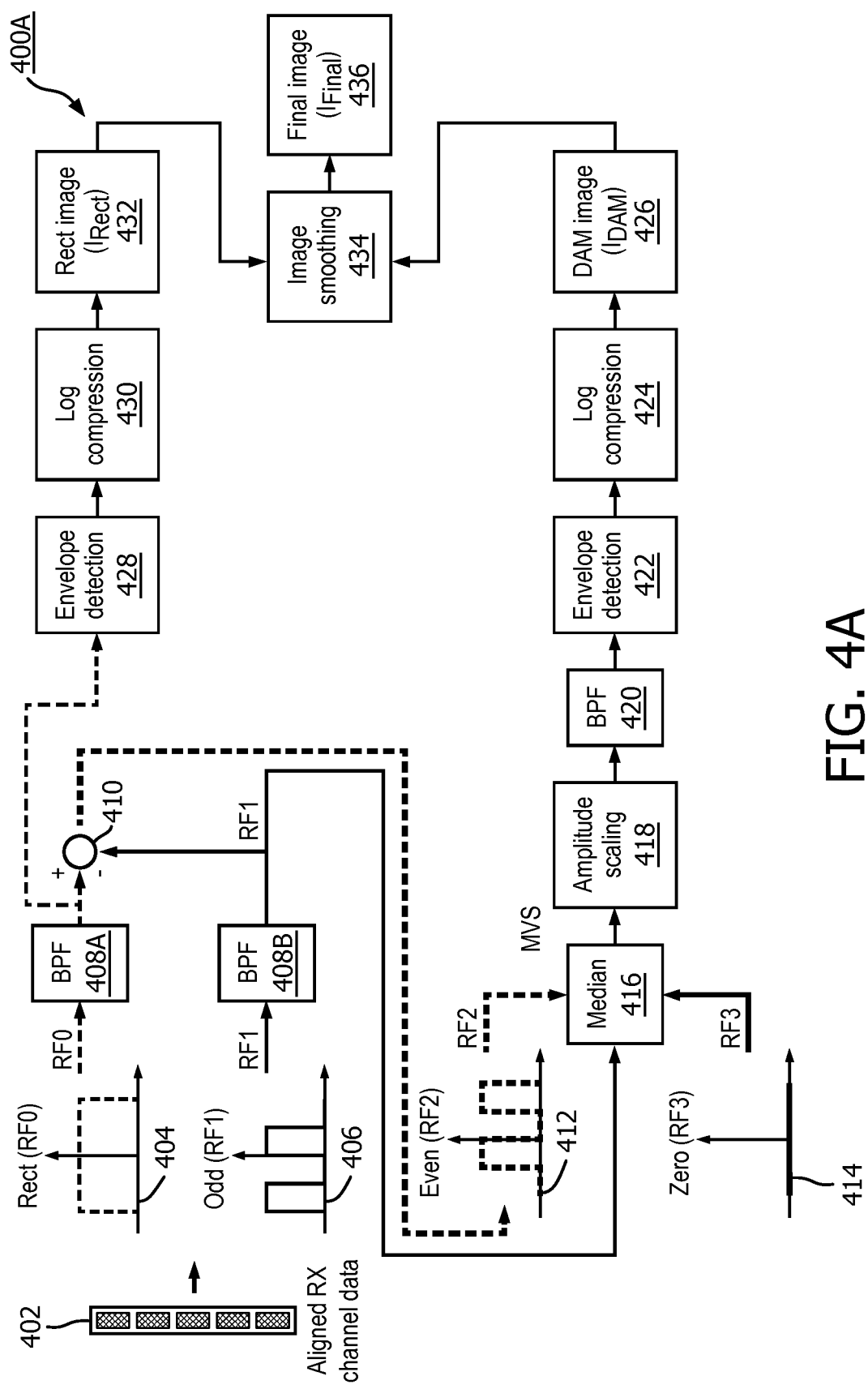
FIG. 4A illustrates an overview of the dual apodization median (DAM) filtering technique according to principles of the present disclosure.

FIG. 4A illustrates an overview 400A of the dual apodization median (DAM) filtering technique according to principles of the present disclosure. The DAM filtering technique may be performed by a signal processor (e.g., signal processor 26) or multiple signal processors in some embodiments. The signal processor may be implemented as hardware, software, or a combination thereof. From the aligned channel data 402 received from a beamformer (e.g., beamformer 22 and/or microbeamformer 16), beamsum radio frequency (RF) signals may be generated by summing aligned channel data with apodization functions as described herein. A first beamsum RF signal RF0 may be obtained by summing aligned channel data with a rectangular apodization function 404 and a second beamsum RF signal RF1 may be obtained by summing aligned channel data with an apodization function with an odd aperture 406 applied. Signals RF0 and RF1 may be passed through a bandpass filters 408A and 408B. The signals RF0 and RF1 may be combined at block 410 where RF1 may be subtracted from RF0 to derive another beamsum RF signal, RF2, which may correspond to a beamsum signal generated from summing aligned channel data 402 with an apodization function with the complementary even aperture 412 applied. Alternatively, RF2 may be obtained by directly summing the aligned channel data 402 with an apodization function with an even aperture applied. However, this may require implementing an additional receive apodization and may require an additional bandpass filter for the signal generated from the additional apodization function.

After obtaining the RF1 and RF2, at block 416, the median value between RF1, RF2, and zero (RF3) 414 may be computed to obtain a new RF signal referred to here as a median value signal MVS. The median value is found for every depth for every lateral location in the ultrasound image. In some embodiments, RF3 may be set to a value other than zero. For example, RF3 may be set to a value close to zero (e.g., 0.1, 0.01, 0.001) to compensate for an offset in the imaging system. The value of RF3 may be pre-set in an ultrasound imaging system and/or may be set by a user via a user interface (e.g., user interface 24).

The beamsum RF signals generated by complementary apodization functions may not sum the aligned channel data from all the channels. This may cause the resulting MVS to have a different amplitude than RF0. In the example shown in FIG. 4A, RF1 and RF2 use only half of the channel data used in RF0, thus the amplitude of RF1 and RF2 may be reduced by approximately a factor of two. Hence, the amplitude of the new RF signal MVS generated by the median operation performed by block 416 is also smaller by a factor of two. This amplitude change may be accounted for by a scaling operation at block 418 on the median value signal MVS. The scaling operation at block 418 may be followed by another bandpass filter 420 to remove any frequency components outside of the transducer bandwidth that may have been introduced by the nonlinear median operation performed by block 416. The bandpass filtered RF signal may then be envelope-detected at block 422 and log-compressed at block 424 to yield a DAM image 426. As shown in FIG. 4A, envelope detection at block 428 and log compression at block 430 are also processes applied to form the original image $I_{Rect}$ 432 (e.g., an image formed without using the DAM technique).

Although the DAM image, $I_{DAM}$ 426 has improved contrast and may be sufficient to replace the original image $I_{Rect}$ 432, some tissue signals may sometimes be lost and thus, the speckle texture may be adversely affected in some cases. This may create a blocky appearance, especially for some in vivo images. To alleviate this possible issue, a multiscale image decomposition image processing technique may optionally be implemented for image smoothing 434. The technique may form a final image $I_{Final}$ 436 by combining the high spatial frequency components of the original image $I_{Rect}$ formed with rectangular apodization and the low spatial frequency components of the DAM image.

Figure 4B:
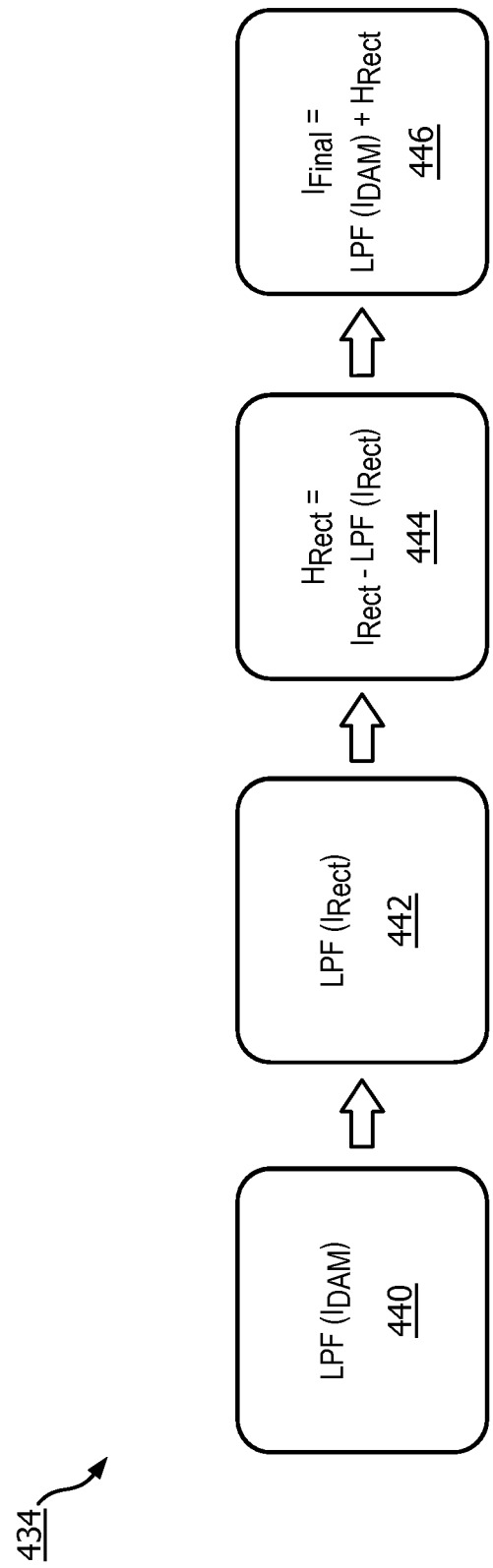
FIG. 4B illustrates the image smoothing of FIG. 4A in more detail.

FIG. 4B illustrates the image smoothing 434 in more detail. The DAM image $I_{DAM}$ 426 is low pass filtered by a spatial low pass filter at Block 440 and the original image $I_{Rect}$ 432 is also low pass filtered by a spatial low pass at Block 442. This may generate low frequency (e.g., blurred) $I_{DAM}$ and $I_{Rect}$ images. Blocks 440 and 442 may be performed in the opposite order or simultaneously. The low-pass filtered original image LPF($I_{Rect}$) is subtracted from the original image to obtain a high frequency original image $H_{Rect}$ at Block 444. Finally, the low pass filtered DAM image $LPF(I_{DAM})$ and $H_{Rect}$ are summed to acquire the final image $I_{Final}$ 436 at Block 446. In other words, the final image may comprise the low frequency components of the $I_{DAM}$ image and the high frequency components (e.g., speckle) of the original image $I_{Rect}$. After image smoothing, the final image may provide enhanced image contrast of the DAM technique while preserving the speckle pattern of the original image.

The functions (e.g., Rect 404 and Odd 406), filters (e.g., 408A, 408B, 420), and/or blocks (e.g., 410, 416, 418) shown in FIGS. 4A and 4B may be implemented in hardware, software, and/or a combination thereof. For example, bandpass filter 408A may be implemented as a circuit or as a digital filter. In another example, block 416 may be implemented as an ASIC or as a software function. Other implementations and combinations of implementations may be used for the functions, filters, and/or blocks shown in FIGS. 4A and 4B.

Figure 5:
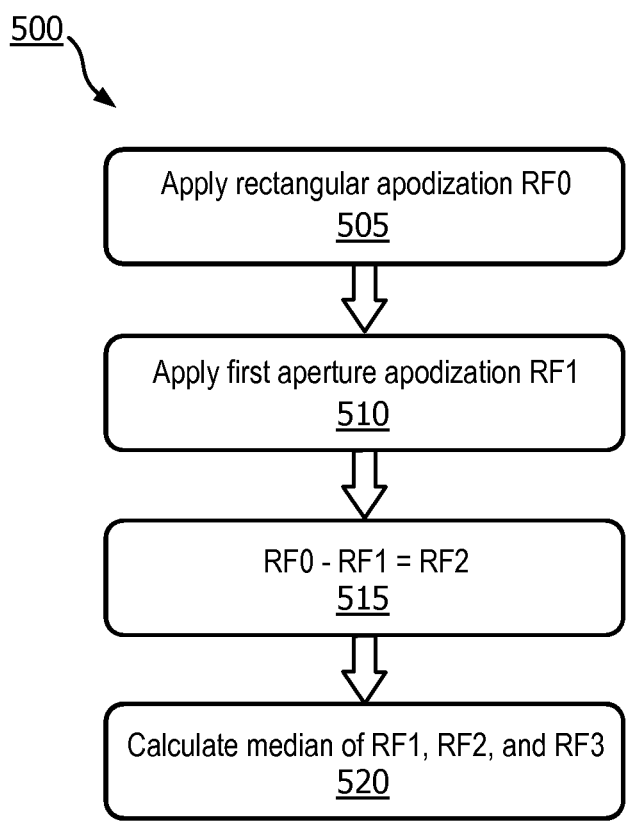
FIG. 5 is a flowchart of a method according to principles of the present disclosure.

FIG. 5 is a flowchart 500 of a method according to principles of the present disclosure. Flowchart 500 summarizes the steps of the DAM filtering technique described above in reference to FIGS. 1-4. The method in FIG. 5 may be performed by a signal processor, such as the signal processor 26 of FIG. 1 and/or the signal processor described in reference to FIG. 4A and/or FIG. 4B. At Step 505, aligned channel data is summed with a rectangular apodization function to obtain signal RF0. The aligned channel data may correspond to data for an ultrasound image. At Step 510, the aligned channel data is summed with an apodization function with a first aperture applied to obtain signal RF1. The first aperture may mask every other element, every two elements, or have a longer period. The longer the period, the more aggressive the DAM filtering will be. Steps 505 and 510 may be performed in reverse order or simultaneously. Bandpass filtering may be applied to RF0 and RF1. At Step 515, signal RF1 is subtracted from RF0 to derive signal RF2. Signal RF2 is equivalent to the aligned channel data summed by an apodization function having an aperture complementary to the first aperture applied. The complementary apertures RF1 and RF2 may be referred to as odd and even apertures, respectively. Alternatively, at Step 515, the aligned channel data may be summed by an apodization function having an aperture complementary to the first aperture applied. In this embodiment, Step 515 may be performed at the same time or prior to Step 505 and/or Step 510. When Step 515 includes directly acquiring the beamsum RF signal from the complementary aperture, Step 505 may be omitted in some embodiments (e.g., when the DAM image will not be combined with an original image). The median value of signals RF1, RF2, and RF3 is calculated at Step 520. Signal RF3 is a constant signal of zero value. Alternatively, RF3 may be a constant signal with a value near zero (e.g., 0.001, 0.01) to compensate for an offset in a system. The median value is calculated for every position and depth in the ultrasound image to generate a median value signal.

After the DAM filtering technique shown in FIG. 5 has been completed, the amplitude of the DAM filtered signal (e.g., all of the calculated median values, the median value signal) may be scaled to compensate for the amplitude reduction introduced by the even and odd aperture apodization functions. The scaled signal may be bandpass filtered to remove any frequency components that may have been introduced by the median operation at Step 520. The bandpass filtered signal may then undergo typical signal processing including envelope detection and log compression to acquire a DAM filtered image. As discussed previously in reference to FIGS. 4A and 4B, the DAM image may be provided and/or a combined original and DAM image may be provided. The image may be provided to a display and/or a computer readable memory for later review.

FIGS. 6-9 show example images generated by conventional techniques and the DAM filtering technique according to principles of the present disclosure. Images generated by the DAM filtering technique may be provided on a display of an ultrasound imaging system (e.g., display 38 in FIG. 1). Images may also be stored to a computer readable medium and/or provided to another display (e.g., a personal computer for post-exam review). The examples described below are illustrative and should not be interpreted to limit the implementations or applications of the DAM filtering technique to the examples disclosed herein.

Figure 6:
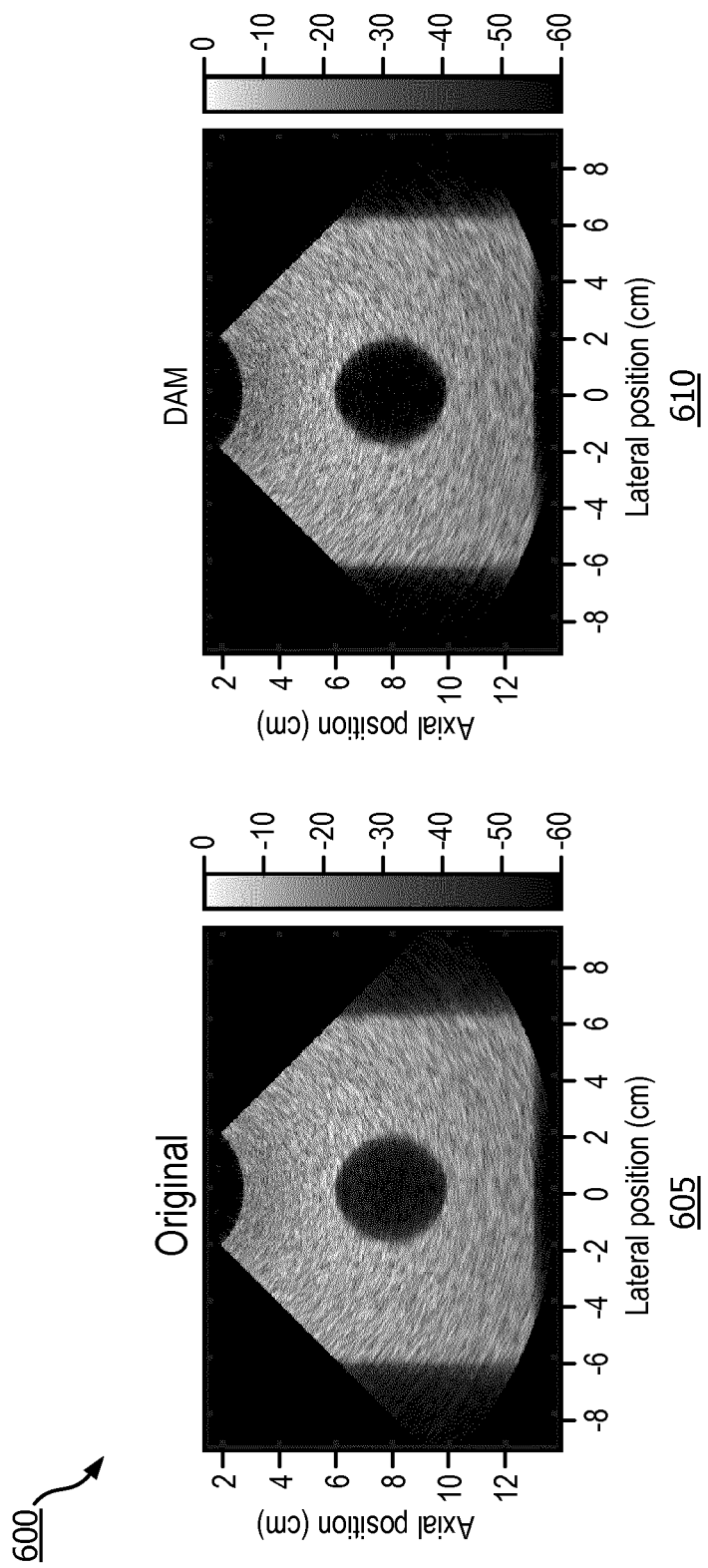
FIG. 6 shows images of a simulated phantom containing a 40 mm-diameter anechoic cyst lesion according to principles of the present disclosure

FIG. 6 shows images 600 of a simulated phantom containing a 40 mm-diameter anechoic cyst lesion. The images were simulated for a 64-element P4-2 phased array. All images are shown on a 60 dB dynamic range. Image 605 was generated using standard delay-and-sum (DAS) beamforming with rectangular RX apodization. Image 610 was obtained by applying the DAM technique. Image contrast enhancement is visible with speckle texture well-preserved. The image smoothing technique described in FIGS. 4A and 4B was not applied.

Figure 7:
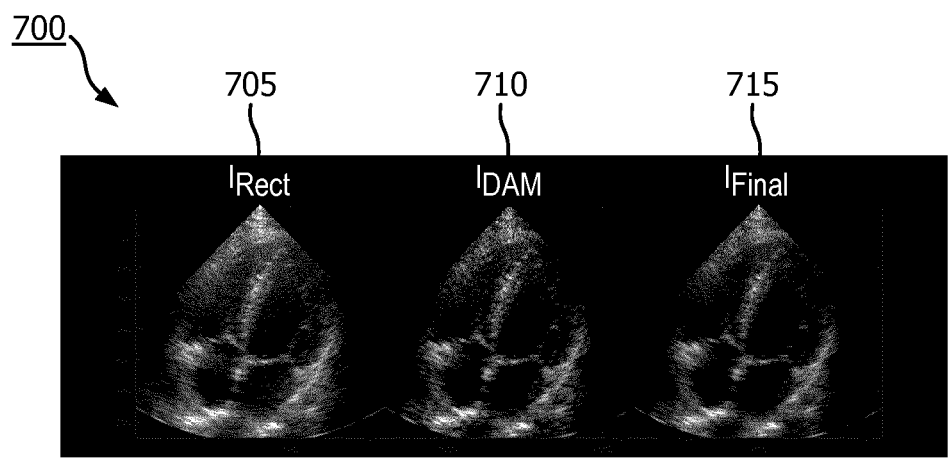
FIG. 7 shows images of an apical 4-chamber view of a heart from a healthy volunteer according to principles of the present disclosure.

FIG. 7 shows images 700 of an apical 4-chamber view of a heart from a healthy volunteer. The data was acquired with an 80-element S5-1 probe. Image 705 was formed with conventional DAS beamforming with rectangular apodization. Image 710 was obtained by applying the DAM technique. Enhancement in image contrast is observed, but some tissue signals have been lost. Right: Image 715 was obtained with the image smoothing technique described in FIGS. 4A and 4B. The smoothness and the details in the original image have been restored while preserving the enhanced contrast provided by the DAM technique.

The DAM technique described herein may address not only off-axis clutter and acoustic reverberation clutter, but also noise introduced by grating lobes. Thus, the DAM technique may be desirable for use in applications where under-sampling may occur, which can introduce and/or enhance grating lobes. For example, intravenous ultrasound (NUS) applications may suffer from under-sampling. Grating lobes may appear in the lumen of the vessel, especially when there are stent struts that are highly reflective.

Figure 8:
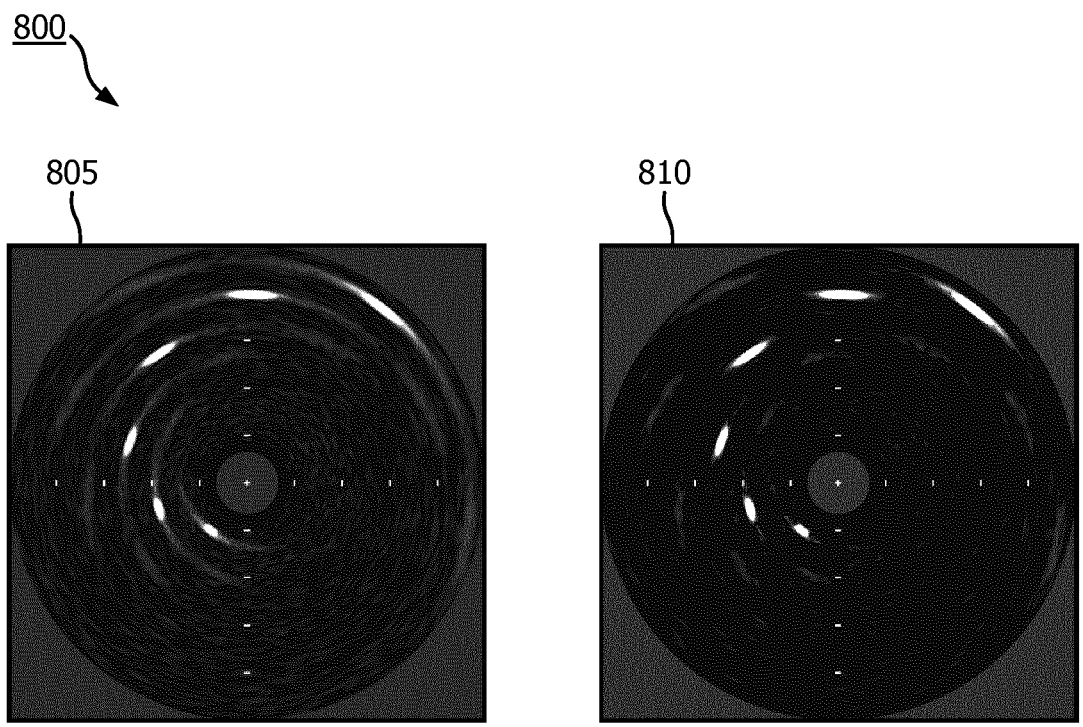
FIG. 8 shows intravenous ultrasound (IVUS) images of a simulated phantom containing six point scatterers and background noise according to principles of the present disclosure.

FIG. 8 shows IVUS images 800 of a simulated phantom containing six point scatterers and background noise. Image 805 was formed with the DAS beamforming and standard apodization. Image 810 was obtained by applying the DAM technique. Image contrast is improved in image 810 compared to image 805 due to incoherent signal (e.g., sidelobes and/or noise) suppression.

Figure 9:
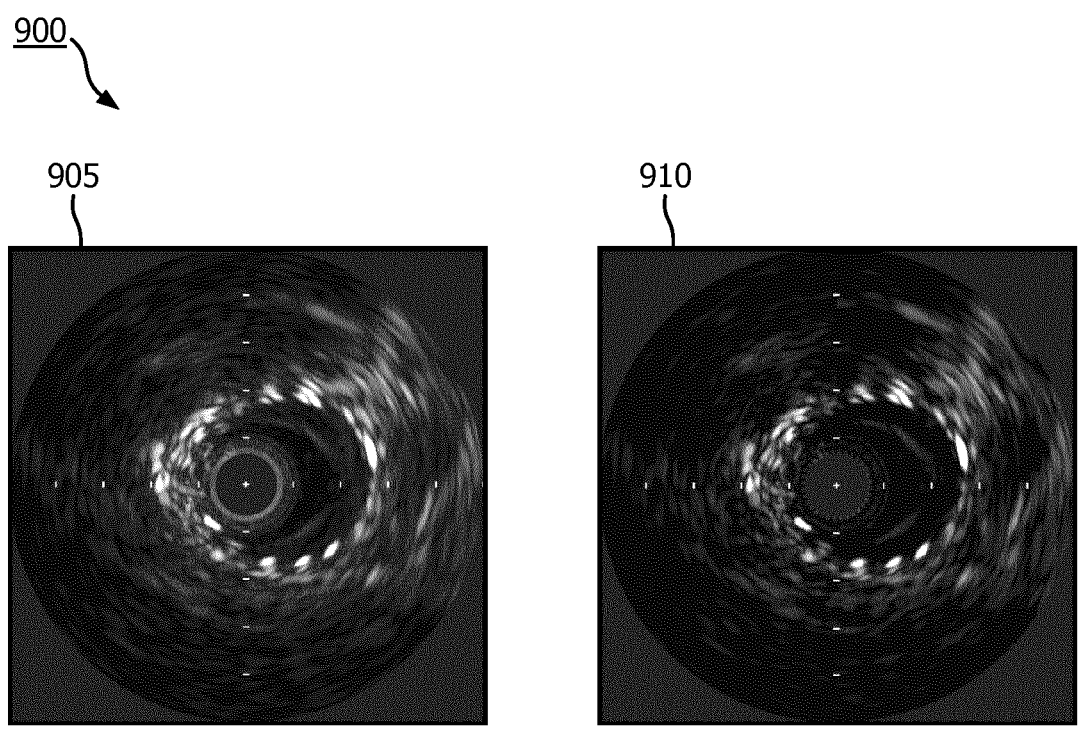
FIG. 9 shows IVUS images of a stent according to principles of the present disclosure.

FIG. 9 shows IVUS images 900 of a stent. Image 905 was formed with conventional DAS beamforming. Image 910 was obtained by applying the DAM technique without image smoothing. Enhancement in image contrast is observed throughout image 910. However, in this example, some grating artifacts inside the lumen add coherently, and therefore were not fully removed by the DAM technique.

According to principles of the disclosure, a DAM filtering technique as described herein may be applied to ultrasound channel data to suppress signals from off-axis sidelobes and/or clutter which may enhance image contrast. This may improve a clinician's ability to locate, recognize, and/or measure anatomical features in the image. The improved contrast may improve a clinician's ability to make diagnoses based on the ultrasound image. The DAM filtering technique may be easier to implement from a hardware perspective than some techniques that require access to per-channel data and/or may be less computationally intensive than some dual apodization techniques.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system has been described with reference to an ultrasound imaging system, the present system may be extended to other imaging techniques. Additionally, the present system may be used to obtain and/or record image information related to, but not limited to renal, testicular, prostate, breast, ovarian, uterine, thyroid, hepatic, lung, musculoskeletal, splenic, nervous, cardiac, arterial and vascular systems, as well as other imaging applications related to ultrasound-guided interventions and other interventions which may be guided by real-time medical imaging. Further, the present system may also include one or more elements which may be used with non-ultrasound imaging systems with or without real-time imaging components so that they may provide features and advantages of the present system.

Further, the present methods, systems, and apparatuses may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging.

Certain additional advantages and features of this invention may be apparent to those skilled in the art upon studying the disclosure, or may be experienced by persons employing the novel system and method of the present invention, chief of which is reduction of noise from off-axis signals by ultrasound imaging systems and method of operation thereof is provided. Another advantage of the present systems and method is that conventional medical imaging systems may be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method comprising:
   obtaining ultrasound data based on ultrasound echoes received by an ultrasound transducer array;
   applying a first apodization function to the ultrasound data to generate a first signal, wherein the first apodization function comprises an odd apodization function;
   applying a third apodization function to the ultrasound data to generate a fourth signal;
   generating a second signal, wherein generating the second signal comprises subtracting the first signal from the fourth signal, wherein subtracting the first signal from the fourth signal is equivalent to applying a second apodization function to the ultrasound data, wherein the second apodization function is an even apodization function complementary to the odd apodization function;
   determining median values of the first signal, the second signal, and a third signal to generate a median value signal, wherein the third signal is a constant value signal, wherein the constant value is zero or near zero; and
   generating an ultrasound image, based at least in part, on the median value signal.

2. The method of claim 1, further comprising applying bandpass filters to the first signal and the fourth signal prior to subtracting.

3. The method of claim 1, further comprising scaling an amplitude of the median value signal.

4. The method of claim 1, further comprising applying a bandpass filter to the median value signal.

5. The method of claim 1, wherein generating the ultrasound image comprises applying envelope detection and log compression to the median value signal.

6. The method of claim 1, further comprising:
generating an original image from the ultrasound data;
applying a first spatial low pass filter to the original image to generate a low frequency original image;
subtracting the low frequency original image from the original image to generate a high frequency original image;
applying a second spatial low pass filter to the ultrasound image to generate a low frequency ultrasound image; and
summing the high frequency original image and the low frequency ultrasound image to generate a final image.

7. The method of claim 1, wherein the first apodization function corresponds to an aperture that masks every other channel of the received ultrasound data.

8. The method of claim 1, wherein the first apodization function corresponds to an aperture that masks multiple adjacent channels of the received ultrasound data.

9. An ultrasound imaging system comprising:
an ultrasound transducer array configured to transmit ultrasound waves and receive ultrasound echoes;
a signal processor operatively coupled to the ultrasound transducer array, wherein the signal processor is configured to:
obtain ultrasound data based on the ultrasound echoes received by the ultrasound transducer array;
apply a first apodization function to the ultrasound data to generate a first signal, wherein the first apodization function comprises an odd apodization function;
apply a third apodization function to the ultrasound data to generate a fourth signal;
generate a second signal;
determine median values of the first signal, the second signal, and a third signal to generate a median value signal, wherein the third signal is a constant value signal,
wherein the constant value is zero or near zero; and
generate an ultrasound image, based at least in part, on the median value signal,
wherein, to generate the second signal, the signal processor is configured to subtract the first signal from the fourth signal,
wherein subtracting the first signal from the fourth signal is equivalent to applying a second apodization function to the ultrasound data,
wherein the second apodization function is an even apodization function complementary to the odd apodization function.

10. The ultrasound imaging system of claim 9, wherein the signal processor is further configured to apply a bandpass filter to the median value signal prior to generation of the ultrasound image.

11. The ultrasound imaging system of claim 9, wherein the signal processor is configured to apply envelope detection and log compression to the median value signal to generate the ultrasound image.

12. The ultrasound imaging system of claim 9, wherein the signal processor is further configured to:
generate an original image from the ultrasound data;
apply a first spatial low pass filter to the original image to generate a low frequency original image;
subtract the low frequency original image from the original image to generate a high frequency original image;
apply a second spatial low pass filter to the ultrasound image to generate a low frequency ultrasound image; and
sum the high frequency original image and the low frequency ultrasound image to generate a final image.

13. The ultrasound imaging system of claim 12, wherein the original image is generated from the fourth signal.

14. The ultrasound imaging system of claim 12, further comprising a display, wherein the display is configured to display at least one of the ultrasound image and the final image.

15. The ultrasound imaging system of claim 9, further comprising a user interface.

16. The ultrasound imaging system of claim 15,
wherein the first apodization function corresponds to an aperture,
wherein a period of the aperture is set by a user via the user interface.

17. The ultrasound imaging system of claim 15, wherein the constant value is set by a user via the user interface.

18. The ultrasound imaging system of claim 9, wherein the signal processor is further configured to apply bandpass filters to the first signal and the fourth signal prior to subtraction.

19. The ultrasound imaging system of claim 9, wherein the third apodization function is a rectangular apodization function.

20. The ultrasound imaging system of claim 9, further comprising:
a plurality of channels operatively coupled to the ultrasound transducer array and configured to transmit channel data based at least in part on the received ultrasound echoes;
a beamformer operably coupled to the plurality of channels and configured to align the channel data,
wherein the ultrasound data comprises the aligned channel data.

* * * * *